(12) United States Patent
Gold et al.

(10) Patent No.: US 10,172,882 B2
(45) Date of Patent: Jan. 8, 2019

(54) PHARMACEUTICAL COMPOSITIONS COMPRISING FERRIC CITRATE AND METHODS FOR THE PRODUCTION THEREOF

(71) Applicant: DEXCEL PHARMA TECHNOLOGIES LTD., Or Akiva (IL)

(72) Inventors: Tomer Gold, Herzliya (IL); Ron Schlinger, Tel Aviv (IL); Yochai Yakovson, Achiya Shilo (IL)

(73) Assignee: DEXCEL PHARMA TECHNOLOGIES LTD., Or-Akiva (IL)

( * ) Notice: Subject to any disclaimer, the term of this patent is extended or adjusted under 35 U.S.C. 154(b) by 0 days.

(21) Appl. No.: 15/315,942

(22) PCT Filed: Jun. 18, 2015

(86) PCT No.: PCT/IL2015/050619
§ 371 (c)(1),
(2) Date: Dec. 2, 2016

(87) PCT Pub. No.: WO2015/198304
PCT Pub. Date: Dec. 30, 2015

(65) Prior Publication Data
US 2017/0106018 A1    Apr. 20, 2017

Related U.S. Application Data

(60) Provisional application No. 62/015,437, filed on Jun. 22, 2014.

(51) Int. Cl.
| | | |
|---|---|---|
| *A61K 33/26* | (2006.01) | |
| *A61K 31/295* | (2006.01) | |
| *A61K 9/16* | (2006.01) | |
| *A61K 9/20* | (2006.01) | |
| *A61K 9/00* | (2006.01) | |
| *A61K 9/28* | (2006.01) | |

(52) U.S. Cl.
CPC ............ *A61K 33/26* (2013.01); *A61K 9/0053* (2013.01); *A61K 9/1635* (2013.01); *A61K 9/1652* (2013.01); *A61K 9/1676* (2013.01); *A61K 9/1682* (2013.01); *A61K 9/2009* (2013.01); *A61K 9/2013* (2013.01); *A61K 9/2027* (2013.01); *A61K 9/2054* (2013.01); *A61K 9/2077* (2013.01); *A61K 9/2866* (2013.01); *A61K 31/295* (2013.01); *A61K 9/2095* (2013.01)

(58) Field of Classification Search
None
See application file for complete search history.

(56) References Cited

U.S. PATENT DOCUMENTS

| | | |
|---|---|---|
| 4,721,709 A | 1/1988 | Seth |
| 4,828,840 A | 5/1989 | Sakamoto |
| 5,505,983 A | 4/1996 | Kamada |
| 5,753,706 A | 5/1998 | Hsu |
| 6,149,943 A | 11/2000 | McTeigue |
| 6,174,442 B1 | 1/2001 | Geisser |
| 6,291,440 B1 | 9/2001 | Andreasen |
| 6,339,080 B1 | 1/2002 | Stockham |
| 6,503,878 B1 | 1/2003 | Schwartz |
| 6,758,161 B2 | 7/2004 | Nohynek |
| 6,779,468 B1 | 8/2004 | Gupta |
| 6,903,235 B2 | 6/2005 | Hsiao |
| 6,977,249 B1 | 12/2005 | Andreasen |
| 7,034,172 B1 | 4/2006 | Friedrich |
| 7,179,939 B2 | 2/2007 | Rangisetty |
| 7,459,569 B2 | 12/2008 | Stockham |
| 7,612,109 B2 | 11/2009 | Geisser |
| 7,767,851 B2 | 8/2010 | Kwok |
| 7,816,404 B2 | 10/2010 | McCall |
| 7,857,977 B2 | 12/2010 | Wash |
| 7,909,929 B2 | 3/2011 | Kimura |
| 8,093,423 B2 | 1/2012 | Chan |
| 8,178,709 B2 | 5/2012 | Nelson |
| 8,252,310 B2 | 8/2012 | Ambuhl |
| 8,298,585 B2 * | 10/2012 | Kakizawa ............ A61K 9/0056 424/464 |
| 8,299,298 B2 | 10/2012 | Chan |
| 8,609,896 B2 | 12/2013 | Kwok |
| 8,754,257 B2 | 6/2014 | Chan |
| 8,754,258 B2 | 6/2014 | Kwok |
| 8,846,976 B2 | 9/2014 | Kwok |
| 8,901,349 B2 | 12/2014 | Kwok |

(Continued)

FOREIGN PATENT DOCUMENTS

| | | |
|---|---|---|
| CN | 1315174 | 10/2001 |
| CN | 1446790 | 5/2005 |

(Continued)

OTHER PUBLICATIONS

US Pharmacopeia <701>.
United States Pharmacopeia 37—National Formulary 32, p. 476-479) (United States Pharmacopeial Convention, Rockville, MD, 2014).
Extended European Search Report cited in application No. 15812000.6-1455, dated Nov. 10, 2017, 7 pages.

*Primary Examiner* — Robert A Wax
*Assistant Examiner* — Melissa S Mercier
(74) *Attorney, Agent, or Firm* — Rothwell, Figg, Ernst & Manbeck, P.C.

(57) ABSTRACT

The present invention relates to a pharmaceutical composition comprising granules which include an inert core coated with ferric citrate. The present invention also provides methods of manufacture thereof and methods of use thereof.

24 Claims, No Drawings

(56) References Cited

U.S. PATENT DOCUMENTS

| | | |
|---|---|---|
| 8,932,648 B2 | 1/2015 | Chan |
| 8,993,748 B2 | 3/2015 | Sacchi |
| 9,050,316 B2 | 6/2015 | Chan |
| 9,095,512 B2 | 8/2015 | Yaginuma |
| 9,096,629 B2 | 8/2015 | Stockham |
| 9,328,133 B2 | 5/2016 | Kwok |
| 9,387,191 B2 | 7/2016 | Le |
| 2005/0163836 A1 | 7/2005 | Fekete |
| 2006/0115539 A1 | 6/2006 | Prasch |
| 2006/0280701 A1 | 12/2006 | Lynch |
| 2007/0011904 A1 | 1/2007 | Sherwood |
| 2009/0280191 A1 | 11/2009 | Endou |
| 2010/0247609 A1 | 9/2010 | Weibel |
| 2010/0255090 A1 | 10/2010 | Rubino |
| 2011/0052722 A1 | 3/2011 | Krebs |
| 2011/0086097 A1 | 4/2011 | Kaufmann |
| 2012/0077888 A1 | 3/2012 | Ramtoola |
| 2012/0121703 A1 | 3/2012 | Fukushima |
| 2012/0115945 A1* | 5/2012 | Le .................. A61K 9/2054 514/502 |
| 2012/0177700 A1 | 7/2012 | Imran |
| 2012/0238622 A1 | 9/2012 | Ando |
| 2012/0288531 A1 | 11/2012 | Tuvia |
| 2013/0039984 A1 | 2/2013 | Kaufmann |
| 2013/0109662 A1 | 5/2013 | Bark |
| 2013/0345303 A1 | 12/2013 | Poradosu |
| 2014/0234416 A1 | 8/2014 | Poradosu |
| 2014/0248363 A1 | 9/2014 | Wagner |
| 2015/0079168 A1 | 3/2015 | Poradosu |
| 2015/0218080 A1 | 8/2015 | Matsuo |

FOREIGN PATENT DOCUMENTS

| | | |
|---|---|---|
| EP | 2161036 | 3/2010 |
| EP | 2 594 277 A1 | 5/2013 |
| WO | WO 1993/000991 | 1/1993 |
| WO | WO 2003/092658 | 11/2003 |
| WO | WO 2007/089571 | 8/2007 |
| WO | WO 2008/058438 | 5/2008 |
| WO | WO 2008/149894 | 12/2008 |
| WO | WO 2011/011541 | 1/2011 |
| WO | WO 2011/013082 | 2/2011 |
| WO | WO 2012/005340 | 1/2012 |
| WO | WO 2015/066593 | 5/2015 |
| WO | WO 2015/110968 | 7/2015 |

* cited by examiner

PHARMACEUTICAL COMPOSITIONS COMPRISING FERRIC CITRATE AND METHODS FOR THE PRODUCTION THEREOF

CROSS REFERENCE TO RELATED APPLICATION

This application is a 35 U.S.C. 371 National Phase Entry Application from PCT/IL2015/050619, filed Jun. 18, 2015, which claims the benefit of U.S. Ser. No. 62/015,437 filed on Jun. 22, 2014, the disclosures of which are incorporated herein in its entirety by reference.

FIELD OF THE INVENTION

The present invention relates to a pharmaceutical composition comprising granules which include an inert core coated with ferric citrate. The present invention also provides methods of manufacture thereof and methods of use thereof.

BACKGROUND OF THE INVENTION

Ferric iron containing compounds are useful in the treatment of a number of disorders, including, but not limited to, hyperphosphatemia and metabolic acidosis. Previous studies and inventions have reported the use of ferric compounds in binding with dietary phosphates, thereby affording the control over phosphate retention in patients suffering from renal failure and associated hyperphosphatemia (U.S. Pat. No. 5,753,706; U.S. Pat. No. 6,903,235; CN 1315174, U.S. Pat. No. 8,093,423). Elevated amounts of phosphate in the blood can be removed by administering ferric iron containing compounds such as ferric citrate. U.S. Pat. No. 5,753,706 discloses compositions consisting of ferric citrate, ferric acetate, and combinations thereof, in a unit dosage of about 500 mg to about 1,000 mg.

WO 2011/011541 discloses ferric citrate tablets comprising 65 wt % to 92 wt % of ferric citrate and 4.5 wt % to 30 wt % binder, wherein at least 80% of the ferric citrate in the tablet is dissolved in a time less than or equal to 60 minutes.

WO 2012/005340 discloses ferric citrate tablets comprising polyvinyl alcohol-polyethylene glycol graft copolymer and polyvinyl alcohol-acrylic acid-methyl methacrylate copolymer. The tablets comprise 70 wt % ferric citrate.

WO 2003/092658 discloses a process for preparing compressed tablets having good mechanical strength. The pharmaceutically active ingredient(s) and excipient(s) are granulated in the presence of a granulating liquid comprising 5-30% microcrystalline cellulose by a kneading or a fluidization spraying process.

WO 2008/149894 discloses a process for producing tablet or capsule comprising a granule, wherein the granule further includes coated core particle. The core is composed of at least 50 wt % microcrystalline cellulose, in which the active pharmaceutical ingredient is sprayed onto the core.

U.S. Pat. No. 6,149,943 discloses a method for preparing a pharmaceutically active particle, which includes about 40 wt % to 75 wt % microcrystalline cellulose as inert core coated with about 25 wt % to 60 wt % pharmaceutically active ingredient. The coating of the microcrystalline cellulose is performed in the absence of a granulation step using a spray coating technique. Further disclosed is a method wherein the coated particles and excipients are compressed to form tablets.

One of the challenges of formulating ferric citrate in solid dosage forms is its relatively high dosage. Thus, in order to prepare dosage forms having properties (e.g., size) compatible with the end user, ferric citrate compositions typically contain high percentages of the active ingredient relative to excipients. Production of such dosage forms containing ferric citrate in high content is associated with problems such as moldability during tableting, cracking, and difficulty in maintaining suitable hardness, while not affecting disintegration and dissolution properties of the dosage forms.

A need in the art exists for ferric citrate compositions that incorporate therapeutically effective doses of the active ingredient to effectively prevent and/or treat hyperphosphatemia and metabolic acidosis, that overcome the aforementioned disadvantages.

SUMMARY OF THE INVENTION

The present invention relates to a pharmaceutical composition comprising granules comprising an inert core coated with ferric citrate and optionally a binder. The present invention also provides methods of manufacture thereof and methods of use thereof.

The present invention is based in part on the unexpected discovery that solid pharmaceutical compositions containing high quantity/load of ferric citrate as an active ingredient can be efficiently manufactured. The high quantity/load of ferric citrate (preferably at least about 50% by weight of the composition) is afforded while allowing the formation of a pharmaceutical dosage form (e.g., a tablet) of a size that is compatible with the end user. Moreover, the solid pharmaceutical composition is characterized by a high in vitro dissolution rate, wherein at least 85%, preferably at least about 90%, more preferably at least about 95% of the drug is released within about 60 minutes, preferably within about 30 minutes, and more preferably within about 15 minutes. The process for manufacturing this solid pharmaceutical composition is a one pot process that is simple, efficient and cost effective to implement.

According to one aspect, the present invention provides a solid pharmaceutical composition comprising: (a) granules comprising an inert core and a layer over said core, said layer comprising ferric citrate in an amount of at least about 50 wt % based on the weight of said composition, and (b) optionally, at least one pharmaceutically acceptable excipient. In one embodiment, the pharmaceutically acceptable excipient is an intra-granular excipient. In another embodiment, the pharmaceutically acceptable excipient is an extra-granular excipient. In yet another embodiment, the pharmaceutical composition comprises both an intra-granular excipient and an extra-granular excipient. In one embodiment, the pharmaceutically acceptable excipient comprises a binder. In another embodiment, the granules are milled.

According to another aspect, the present invention provides a solid pharmaceutical composition comprising: (a) milled granules comprising an inert core and a layer over said core, said layer comprising ferric citrate in an amount of at least about 50 wt % based on the weight of said composition, and optionally a binder, and (b) optionally, at least one pharmaceutically acceptable excipient.

According to some embodiments, the amount of ferric citrate is at least about 60% by weight of the composition. In other embodiments, the amount of ferric citrate is at least about 70% by weight of the composition. The high load of ferric citrate in the composition allows for the incorporation of relatively high dose of the active ingredient, e.g., at least about 500 mg to at least about 1,500 mg ferric citrate per dosage form while maintaining a size that is compatible with the end user.

According to some embodiments, the granules are prepared by applying a composition comprising ferric citrate and optionally a binder over the inert core. The application of a composition comprising ferric citrate over the inert core may be performed as is known in the art, for example using spray coating. The granules are optionally milled. The granules may further be blended with at least one pharmaceutically acceptable excipient, and further processed to produce a solid pharmaceutical dosage form, e.g., a tablet.

According to some embodiments, the inert core comprises microcrystalline cellulose (e.g., AVICEL®).

According to certain embodiments, the weight ratio between the inert core and the ferric citrate coating layer is about 1 to about 8-300 (1:8 to 1:300). In other embodiments, the weight ratio between the inert core and the ferric citrate coating layer is about 1 to about 8-150 (1:8 to 1:150). In additional embodiments, the weight ratio between the inert core and the ferric citrate coating layer is about 1 to about 100-150 (1:100 to 1:150).

According to other embodiments, the composition further comprises at least one excipient selected from the group consisting of a binder, a disintegrating agent, a filler, an anti-tacking agent, a lubricant, a glidant, a surfactant, a plasticizer or any combination thereof with each possibility representing a separate embodiment of the present invention. These excipients are preferably blended with the granules as intra-granular and/or extra-granular excipients, so as to form the solid dosage forms of the invention. It is understood that a binder may be present in the ferric citrate layer (i.e., intra-granular excipient), or as an extra-granular excipient, or a combination thereof. Each possibility represents a separate embodiment of the present invention. According to other embodiments, the ferric citrate layer further comprises a binder. In one embodiment, the binder is povidone (PVP). In another embodiment, the binder is starch, pregelatinized starch or a combination thereof. Each possibility represents a separate embodiment of the present invention.

Any pharmaceutically acceptable excipients can be used in the compositions of the present invention. In one embodiment, the filler/diluent is microcrystalline cellulose. In another embodiment, the disintegrating agent is crospovidone. In another embodiment, the glidant is colloidal silicon dioxide. In another embodiment, the lubricant is sodium stearyl fumarate. In yet another embodiment, the lubricant is calcium stearate. Additional excipients suitable for use in the context of the present invention are described herein below.

According to some embodiments, the composition of the present invention has an in vitro dissolution profile at pH of about 1 to about 7, preferably pH of about 4 to about 7, in which at least about 85% of the drug is released from the composition within about 60 minutes, preferably within about 30 minutes, and more preferably within about 15 minutes. In certain embodiments, the composition has an in vitro dissolution profile, when measured in a type II Paddle dissolution apparatus in McIlvaine buffer 98% (pH 4.0), in which at least about 85% of the drug/pharmaceutical composition is released within about 60 minutes, preferably within about 30 minutes, and more preferably within about 15 minutes. In some embodiments, at least about 90% of the drug/pharmaceutical composition is released within about 60 minutes, preferably within about 30 minutes, and more preferably within about 15 minutes. In other embodiments, at least about 95% of the drug/pharmaceutical composition is released within about 60 minutes, preferably within about 30 minutes, and more preferably within about 15 minutes.

According to some embodiments, the composition is in a form suitable for oral administration. In accordance with these embodiments, the composition is in a form selected from the group consisting of a tablet, a capsule, a pill, a powder and a pellet. Each possibility represents a separate embodiment of the present invention. In further embodiments, the composition may be filled into capsules or sachet for oral administration. In other embodiments, the composition (e.g., in the form of a powder) may be mixed with a liquid thereby forming a suspension or solution for oral administration. In one currently preferred embodiment, the present invention is directed to a solid dosage form in the form of a tablet. According to some embodiments, the present invention relates to a tablet obtainable by compressing the pharmaceutical composition as described herein.

According to other embodiments, the composition further comprises at least one coating layer. In one embodiment, the coating layer is an immediate release coating. In certain embodiments, the composition further comprises at least one coating layer over the ferric citrate layer.

According to some embodiments, the composition comprises residual amount of water in an amount of about 1-20% by weight of the composition, e.g., about 5-20% by weight of the composition. In certain embodiments, the granules comprise residual amount of water in an amount of about 1-20% by weight of the composition, e.g., about 5-20% by weight of the composition prior to being compressed into a tablet.

According to some embodiments, the composition of the present invention has a BET (Brunauer Emmett Teller) active surface area of less than about 10 sq. m/g, preferably less than about 5 sq. m/g, and more preferably less than about 3 sq. m/g.

According to yet another aspect, the present invention provides a method for preparing granules comprising ferric citrate, the method comprising the steps of: (a) dissolving ferric citrate and optionally a binder in an aqueous medium to obtain a solution; (b) applying the solution obtained in step (a) onto an inert core so as to obtain granules; and (c) optionally milling the granules. In one embodiment, step (a) further includes the use of a binder. In another embodiment, the method further includes the step of drying the granules obtained in step (b) or the milled granules obtained in step (c). In yet another embodiment, the optional milling step is performed.

According to some embodiments, the method further comprises the step of blending the granules with at least one pharmaceutically acceptable excipient. The at least one pharmaceutically acceptable excipient may be an intra-granular and/or an extra-granular excipient.

According to other embodiments, the step of dissolving the ferric citrate further includes addition of one or more of a buffering agent, wetting agent or surfactant.

According to certain embodiments, the aqueous medium is water. In further embodiments, the water is hot water. According to some embodiments, the hot water is at a temperature of between about 40° C. to about 80° C. According to other embodiments, the solution is kept heated at above about 80° C. throughout the process.

According to certain embodiments, the step of applying the solution obtained in step (a) onto an inert core comprises the use of spray coating.

According to some embodiments, the granules are milled to form a powder having a mean particle size of less than about 400 microns. In various embodiments, the granules are milled to form a powder wherein about 50% of the particles have a particle size of less than about 75 microns.

According to another aspect, the present invention further provides a method for preparing a composition comprising granules comprising ferric citrate, the method comprising the step of applying at least one coating layer onto said composition.

According to some embodiments, the present invention provides a method for preparing a tablet comprising ferric citrate, the method comprising the steps of: (a) dissolving ferric citrate and optionally a binder in an aqueous medium to obtain a solution; (b) applying the solution obtained in step (a) onto an inert core so as to obtain granules; (c) optionally milling the granules; (d) optionally drying the granules obtained in step (b) or the milled granules obtained in step (c); (e) blending the granules obtained in step (b) or the milled granules obtained in step (c) or the dried granules obtained in step (d) with at least one pharmaceutically acceptable excipient; and (f) compressing the blend of step (e) to obtain a tablet comprising ferric citrate. In one embodiment, step (a) further includes the use of a binder. In another embodiment, the optional drying step is performed. In yet another embodiment, the optional milling step is performed.

According to yet another aspect, the present invention provides a method for treating a disorder or a medical condition in a subject, selected from the group consisting of renal insufficiency, renal failure, hyperphosphatemia, metabolic acidosis, calcium phosphate deposition, calcification of soft tissue, kidney stones, elevated serum calcium levels and anemia, the method comprising the step of administering to a subject in need thereof a pharmaceutical composition comprising ferric citrate as described herein.

According to some embodiments, the subject is a mammal. According to other embodiments, the subject is a human. According to further embodiments, the administration route is oral.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PRESENT INVENTION

Ferric Citrate Compositions

According to some aspects and embodiments, the present invention provides a solid pharmaceutical composition comprising: (a) granules comprising an inert core and a layer over said core, said layer comprising ferric citrate in an amount of at least about 50 wt % based on the weight of said composition and optionally a binder; and (b) optionally, at least one pharmaceutically acceptable excipient.

According to other aspects and embodiments, the present invention provides a solid pharmaceutical composition comprising: (a) milled granules comprising an inert core and a layer over said core, said layer comprising ferric citrate in an amount of at least about 50 wt % based on the weight of said composition, and optionally a binder; and (b) optionally, at least one pharmaceutically acceptable excipient.

According to certain aspects and embodiments, provided herein is a solid pharmaceutical composition comprising granules comprising an inert core and a layer comprising ferric citrate which is applied to the inert core such that the amount of ferric citrate is at least about 50 wt % based on the weight of said composition. The composition of the present invention may optionally comprise at least one pharmaceutically acceptable excipient which may be an intra-granular excipient, an extra-granular excipient or a combination thereof. Each possibility represents a separate embodiment of the present invention. In various embodiments, the granules are milled.

The solid pharmaceutical compositions of the present invention exert surprisingly advantageous properties including improved dissolution and stability. The present invention demonstrates for the first time that by applying a ferric citrate solution over an inert core to obtain granules, a dosage form (e.g., tablet) having increased solubility and stability can be obtained, in comparison to a dosage form prepared from conventional granules which are not prepared by applying a ferric citrate solution over an inert core.

The granules, according to the principles of the present invention, are prepared by applying (e.g. using spray coating) a composition comprising ferric citrate and optionally a binder over the inert core so as to obtain granules. The granules are optionally milled. The granules are then optionally blended with at least one pharmaceutically acceptable excipient.

The granules thus obtained may further be processed as is known in the art to a solid dosage form particularly suitable for oral administration. The solid dosage form may be in a form selected from the group consisting of a tablet, a capsule (including a hard shell capsule or a soft shell capsule), a pill, a powder, and a pellet. Each possibility represents a separate embodiment of the present invention. In an exemplary embodiment, the present invention provides a powder suitable for oral administration, said powder can be filled into capsules or sachet to be administered as sprinkle dosage form or mixed with a liquid prior to administration thereby forming a suspension or solution. In other embodiments, the present invention provides a tablet suitable for oral administration. In certain embodiments, the tablet disclosed herein comprises granules comprising an inert core and a layer over said core, said layer comprising ferric citrate in an amount of at least about 50 wt % based on the weight of said composition, and further comprises at least one binder and at least one pharmaceutically acceptable excipient. In other embodiments, the present invention provides a tablet comprising milled granules comprising an inert core and a layer over said core, said layer comprising ferric citrate in an amount of at least about 50 wt % based on the weight of said composition, and further comprising at least one binder and at least one pharmaceutically acceptable excipient. In some embodiments, the tablet is able to sustain compression at a level of about 40 to about 300 N, for example about 100 to about 300 N, preferably about 150 to about 300 N. In certain embodiments, the tablet is further characterized by having friability of less than about 1%, for example about 0.2% to about 1%. In additional embodiments, the disintegration of said tablet as measured in e.g. USP general method <701> is less than about 60 minutes, for example about 50, 40, 30, 20 or 10 minutes. In one embodiment, the disintegration of the tablet is performed in less than about 50 seconds.

The active ingredient, ferric citrate, can be prepared in accordance with any method known in the art or obtained from any source, including any commercial source. It is contemplated that any pharmaceutically acceptable form of ferric citrate including, but not limited to, solvates (e.g. hydrates), polymorphs, and pseudopolymorphs thereof are within the scope of the present invention. According to some embodiments, the amount of ferric citrate is at least about 60% by weight of the composition. In other embodiments, the amount of ferric citrate is at least about 70% by weight of the composition.

According to certain aspects and embodiments, the weight ratio between the inert core and the coating layer is about 1 to about 8-300 (1:8 to 1:300). According to some embodiments, the weight ratio between the inert core and the coating layer is about 1 to about 8-150 (1:8 to 1:150), preferably is about 1 to about 100-150 (1:100 to 1:150), or about 1 to about 9-120 (1:9 to 1:120). The compositions of the present invention allow for high load of active ingredient vs. inactive excipients, thus enabling incorporation of a high dosage of ferric citrate e.g., at least about 500 mg to at least about 1,500 mg per dosage form, for example at least about 500, 600, 700, 800, 900, 1,000, 1,100, 1,200, 1,300, 1,400 or 1,500 mg while keeping the dosage form at a size that is compatible with the end user.

According to some embodiments, the inert core comprises microcrystalline cellulose in an amount of about 0.1 wt % to about 50 wt % based on the weight of said composition. According to other embodiments, the inert core comprises microcrystalline cellulose in an amount of about 1 wt % to about 50 wt % based on the weight of said composition. According to yet other embodiments, the inert core comprises microcrystalline cellulose in an amount of about 5 wt % to about 20 wt % based on the weight of said composition. According to additional embodiments, the inert core comprises microcrystalline cellulose in an amount of about 5 wt % based on the weight of said composition.

The inert core of the compositions described herein can be comprised of any pharmaceutically inert compound, e.g., a filler. The inert core onto which the ferric citrate and optional binder is applied is usually comprised of sugars and starch (e.g. nonpareil seeds) or cellulosic materials, ionic compositions (e.g. calcium dibasic phosphate) or combinations thereof, for example sugar derivatives such as lactose, sucrose, hydrolyzed starch (maltodextrins) or celluloses or mixtures thereof. A currently preferred excipient for the inert core is microcrystalline cellulose (AVICEL®). Any pharmaceutically acceptable AVICEL® grade can be used in the context of the invention, e.g., AVICEL® 101, AVICEL® 102 and the like.

According to some embodiments, the binder in the ferric citrate layer is selected from the group consisting of povidone (PVP), hydroxypropyl cellulose (HPC), hydroxypropylmethyl cellulose (HPMC), sodium alginate, alginic acid, guar gum, acacia gum, xanthan gum, carbopol, cellulose gum (carboxymethyl cellulose), ethyl cellulose, maltodextrin, PVP/VA (vinylpyrrolidone/vinyl acetate copolymer), microcrystalline cellulose, starch (partially or fully pregelatinized starch such as starch 1500) and methyl cellulose, or any combination thereof among others. Each possibility represents a separate embodiment of the invention. A currently preferred binder is povidone (PVP).

In addition to the binder in the ferric citrate layer, the compositions of the invention may further include a binder as an extra-granular excipient. Any one of the binders described above is suitable for use as an extra-granular excipient. In some embodiments, a binder is present as an intra-granular excipient, an extra-granular excipient or a combination thereof. Each possibility represents a separate embodiment of the present invention.

According to other embodiments, the composition further comprises at least one excipient selected from the group consisting of a binder, disintegrating agent, a filler, an anti-tacking agent, a lubricant, a glidant, a surfactant, a plasticizer or any combination thereof. The excipient may by intra-granular, i.e., it is incorporated in the granules of the invention. In alternative embodiments, the excipient may be extra-granular, i.e., it may be blended with the granules of the invention as an extra-granular excipient.

Any pharmaceutically acceptable filler/diluent can be used in the compositions of the present invention. Non-limiting examples of suitable fillers include sugars (such as lactose, glucose, fructose, or sucrose), microcrystalline cellulose, dicalcium phosphate, a sugar alcohol (such as sorbitol, mannitol, maltitol, lactitol, xylitol, isomalt, and erythritol), a hydrogenated starch hydrolysate, a starch (such as corn starch, or potato starch), or sodium carboxymethylcellulose, ethylcellulose, cellulose acetate and any combination thereof. Each possibility represents a separate embodiment of the present invention. In one currently preferred embodiment, the filler/diluent is microcrystalline cellulose.

Any pharmaceutically acceptable disintegrant can be used in the compositions of the present invention. Non-limiting examples of suitable disintegrants include low-substituted carboxymethyl cellulose sodium, cross-linked polyvinyl pyrrolidone (crospovidone), sodium starch glycolate, cross-linked sodium carboxymethyl cellulose, pregelatinized starch (starch 1500), microcrystalline starch, water insoluble starch, calcium carboxymethyl cellulose, low substituted hydroxypropyl cellulose, magnesium aluminum silicate, and any combination thereof. Each possibility represents a separate embodiment of the present invention. In one currently preferred embodiment, the disintegrating agent is crospovidone (cross-linked povidone).

Any pharmaceutically acceptable glidant can be used in the compositions of the present invention. Non-limiting examples of suitable glidants include corn starch, silica derivatives, including silicon dioxide, silica anhydrous, talc and any combination thereof. Each possibility represents a separate embodiment of the present invention. In one currently preferred embodiment, the glidant is colloidal silicon dioxide.

Any pharmaceutically acceptable lubricant can be used in the compositions of the present invention. Non-limiting examples of suitable lubricants include magnesium stearate, calcium stearate, oleic acid, caprylic acid, stearic acid, magnesium isovalerate, calcium laurate, magnesium palmitate, behenic acid, glyceryl behenate, glyceryl stearate, sodium stearyl fumarate, potassium stearyl fumarate, zinc stearate, sodium oleate, sodium stearate, sodium benzoate, sodium acetate, sodium chloride, talc, solid polyethylene glycols, hydrogenated vegetable oil, and any combination thereof. Each possibility represents a separate embodiment of the present invention. In one currently preferred embodiment, the lubricant is sodium stearyl fumarate. In another currently preferred embodiment, the lubricant is calcium stearate.

Non-limiting examples of anti-tacking agents that may optionally be employed include magnesium stearate, calcium stearate, stearic acid, talc, colloidal silicon and the like among others. Each possibility represents a separate embodiment of the invention.

Non-limiting examples of plasticizers that may optionally be employed include dibutyl sebacate, polyethylene glycol, polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol among others. Each possibility represents a separate embodiment of the invention.

The surfactants that may optionally be employed in the present invention may be non-ionic, anionic or cationic. Typically, surfactants may have one lipophilic and one hydrophilic group in the molecule. The surfactant may optionally comprise one or more of soaps, detergents, emulsifiers, dispersing and wetting agents. More specifically, surfactants may optionally comprise, for example, one or more of stearyl triethanolamine, sodium lauryl sulfate, sodium taurocholate, laurylaminopropionic acid, lecithin, benzalkonium chloride, benzethonium chloride and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose among others. Each possibility represents a separate embodiment of the invention.

According to other embodiments, the composition may optionally further comprises additional excipients, provided that such additional excipients do not interfere or adversely affect the desired biological activity of the composition of the present invention. For example: sweetener (such as acesulfame potassium and sucralose), flavorant (such as citric acid powder, strawberry flavor, menthol, orange or mint flavor, or a combination thereof), breath-freshener and/or colorant (pigment or dye). Flavorants and sweeteners are particularly useful when the active ingredient has a bitter taste, the masking of which would increase patient compliance as ferric citrate may have an unpleasant "iron" taste.

According to additional embodiments, the composition further comprises at least one coating layer over the ferric citrate layer or alternatively over the entire solid dosage form, for example, a film coating. The coating layer is preferably an immediate release coating, but may also be an extended, controlled or delayed release coating. In one embodiment, when a functional coating such as extended, controlled or delayed release is applied to the granules, the step of milling the granules is avoided. The coating over the ferric citrate layer or over the entire solid dosage form, may comprise polymers which are preferably water soluble (including cellulosic polymers such as hydroxypropyl methylcellulose (HPMC) or hydroxypropyl cellulose (HPC)), polyvinyl alcohol (PVA), polyvinylpyrrolidone (PVP), or polyethylene glycol, among others. Sugar/lactose coating is also optional. Each possibility represents a separate embodiment of the invention. In one currently preferred embodiment, the coating layer comprises hydroxypropyl methylcellulose (HPMC) which does not contain iron compounds.

According to some embodiments, the coating layer may further include a taste-masking coating. The taste-masking coating may comprise, but is not limited to, one or more of the following polymers: water insoluble polymers (water insoluble cellulosic polymers such as ethylcellulose), acrylate polymers ((meth)acrylate based polymers such as Eudragit® RS, Eudragit® RL and Eudragit® EPO) and water soluble polymers (water soluble cellulosic polymers such as hydroxypropylcellulose (HPC) and hydroxypropyl methylcellulose (HPMC)) or mixtures thereof among others. Each possibility represents a separate embodiment of the invention.

According to various embodiments, the composition comprises residual amount of water in an amount of about 1-20% by weight of the composition, preferably about 5-20% by weight of the composition. In certain embodiments, the granules comprise residual amount of water in an amount of about 1-20% by weight of the composition, e.g., about 5-20% by weight of the composition.

According to certain embodiments, the compositions of the present invention have an immediate release profile. The compositions have an in vitro dissolution profile wherein at least about 85% of the drug is released from the composition within about 60 minutes, preferably within about 30 minutes, and more preferably within about 15 minutes. In one embodiment, at least about 90% of the drug is released within about 60 minutes, preferably within about 30 minutes, and more preferably within about 15 minutes. In another embodiment, at least about 95% of the drug is released within about 60 minutes, preferably within about 30 minutes, and more preferably within about 15 minutes.

The dissolution tests of the compositions may be performed in any suitable apparatus, such as a type II Paddle Dissolution Apparatus (e.g. Distek Evolution 6100), using a rotation speed of 100 rpm and temperature of 37° C.±0.5° C. The dissolution media may be, for example McIlvaine buffer 98% (pH 4.0). The release can be determined using a UV-VIS instrument such as Agilent 8453 UV-VIS, 360 nm with 600 nm background. Alternatively, the dissolution tests of the compositions may be performed in USP Apparatus II (Paddle) (VanKel or Distek or equivalent) using a rotation speed of 100 rpm and temperature of 37° C.±0.5° C. The dissolution media may be, for example McIlvaine buffer pH 4 or 0.1N HCl or acetate buffer pH 4.5 or phosphate buffer pH 6.8 or EDTA solution; with samples filtration: 20 mic cannula style filter. Measurements may be performed using e.g. UV-VIS spectrophotometer or by HPLC system using Reverse Phase C18 column.

According to some embodiments, the coated granules (inert core coated with ferric citrate) may have a BET (Brunauer Emmett Teller) active surface area of less than about 10 sq. m/g, preferably less than about 5 sq. m/g, and more preferably less than about 3 sq. m/g. BET analysis can be performed according to the standards set forth in the United States Pharmacopeia (USP) (United States Pharmacopeia 37—National Formulary 32, p. 476-479) (United States Pharmacopeial Convention, Rockville, Md., 2014).

According to various embodiments, the present invention provides a stable composition comprising ferric citrate. In some embodiments, the composition of the present invention is stable even after accelerated storage conditions (e.g. 40° C. and 75% relative humidity). In one embodiment, the composition provides an in vitro dissolution profile wherein at least about 85%, preferably at least about 90% of the drug is released from the composition within about 60 minutes, preferably within about 30 minutes, and more preferably within about 15 minutes after three months at 40° C. and 75% relative humidity, using any of the dissolution tests described herein.

Process for Manufacturing Ferric Citrate Compositions

According to some embodiments, the present invention provides a method for preparing granules comprising ferric citrate, the method comprising the steps of: (a) dissolving ferric citrate and optionally a binder in an aqueous medium, (e.g., water, preferably hot water) to obtain a solution; (b) applying the solution obtained in step (a) onto an inert core so as to obtain granules; and (c) optionally milling the granules. According to other embodiments, the present invention provides a method for preparing a tablet, the method further comprising the steps of: (d) optionally drying the granules obtained in step (b) or the milled granules obtained in step (c); (e) blending the granules obtained in step (b) or the milled granules obtained in step (c) or the dried granules obtained in step (d) with at least one pharmaceutically acceptable excipient; and (f) compressing the blend of step (e) to obtain a tablet comprising ferric citrate. The at least one pharmaceutically acceptable excipient which is blended with the granules or the milled granules or the dried granules may be an intra-granular excipient, an extra-granular excipient, or a combination thereof.

In one embodiment, the method of the present invention comprises step (d) of drying the granules obtained in step (b) or the milled granules obtained in step (c) such that the granules comprise residual amount of water in an amount of about 1-20% by weight of the composition, e.g., about 5-20% by weight of the composition. In accordance with these embodiments, the residual amount of water of about 1-20%, for example about 5-20% is present in the granules prior to them being further processed such as for example, compressed into a tablet. In particular embodiments, the method of the present invention does not include a step of post-tableting drying.

According to other embodiments, the step of dissolving the ferric citrate further includes addition of one or more of a buffering agent for controlling and/or adjusting the pH value of the solution. Further, wetting agents or surfactants may be added. Examples of suitable surfactants include, but are not limited to, non-ionic, anionic or cationic surfactants as described above.

According to some embodiments, the ferric citrate and optional binder are dissolved in hot water which is at a temperature of between about 30° C. to about 80° C., more preferably between about 40° C. to about 80° C. In one currently preferred embodiment, the solution is kept heated to above about 80° C., for example about 80° C. to about 90° C., throughout the process.

The hot solution may then be applied, for example by spray coating, onto the inert core. Non-limiting examples for spray coating apparatus which may be employed in the present invention include rotary disks, single-fluid high pressure swirl nozzles, two-fluid nozzles or ultrasonic nozzles, Single stage dryer, Two stage dryer, Horizontal dryer, Fluidized spray coater (e.g., TURBOJET), Multi stage drier, Compact spray dryer, Integrated filter drier, FILTER-MAT® dryer, including, e.g., Glatt, Gea-Niro, BWI Hüttlin, Allgaier among others. Each possibility represents a separate embodiment of the invention.

According to some embodiments, the final granules are milled to form a powder having a mean particle size of about 400 microns or less, for example about 400, 300, 200, or 100 microns. In certain embodiments, at least about 50% of the granules have a particle size of less than about 75 microns, for example about 25-75 microns, preferably about 45-75 microns. The equipment used to mill the granules include for example, fluid energy milling, impact milling, cutting milling, compression milling, screening milling, tumbling milling, and oscillating milling. Each possibility represents a separate embodiment of the invention. Sieving of the milled granules may also be performed using vibrators or shakers as is known in the art.

According to some embodiments, the method further comprises the step of blending/mixing said granules with at least one pharmaceutically acceptable excipient, which may be an intra-granular excipient, an extra-granular excipient, or a combination thereof. The mixing process can be achieved using any suitable type of mixer or blender. Non-limiting examples include: simple paddle mixer, ribbon and/or tumbling mixers, plow blenders and drum agglomerators, V-blenders, double cone blenders, slant cone blenders, twin shell blenders, e.g., PATTERSON KELLEY V Blenders, GEMCO double cone blenders, diffusion blender and the like among others. Each possibility represents a separate embodiment of the present invention.

According to some embodiments, the granules mixed with at least one pharmaceutically acceptable excipient or the milled granules mixed with at least one pharmaceutically acceptable excipient may optionally be compressed into a tablet. The tableting process can be achieved using any suitable tableting equipment. Non-limiting examples include: mini press, single or double punch or rotary tablet press such as Killian, Korsch, Colton, Manesty, Stokes, Vector and the like among others.

According to some embodiments, the method for preparing the dosage forms of the invention further comprises the step of applying at least one coating layer onto said dosage form.

Therapeutic Uses

According to certain embodiments, the present invention provides a method for treating a disorder and/or medical condition in a subject, selected from the group consisting of renal insufficiency, renal failure, hyperphosphatemia and/or metabolic acidosis, calcium phosphate deposition, calcification of soft tissue, kidney stones, elevated serum calcium levels and anemia. The method comprises the step of administering to a subject in need thereof a ferric citrate pharmaceutical composition as described herein.

As used herein, the term "administering" refers to bringing in contact with the composition of the present invention. Administration can be accomplished to cells or tissue cultures, or to living organisms, for example mammals, preferably humans. According to other embodiments, the administration route is oral.

The terms "treating" or "treatment" are interchangeable and refer to any one or more of reduction in the progress of the condition (including the rate of progress), a halt in the rate of progress, amelioration of the condition and cure of the condition. Treatment as a prophylactic measure (i.e. prophylaxis) is also included. "Treating" and "treatment" also refer to reducing the symptoms associated with the condition that is being treated.

The terms "renal insufficiency" and/or "renal failure" refer to subjects having acute, chronic and/or end-stage renal failure. The subject may optionally be on dialysis treatment which may be hemodialysis or peritoneal dialysis.

According to another aspect, the present invention provides use of a composition as described herein, for the manufacture of a medicament for treating a disorder and/or medical condition selected from the group consisting of renal insufficiency, renal failure, hyperphosphatemia and/or metabolic acidosis, calcium phosphate deposition, calcification of soft tissue, kidney stones, and elevated serum calcium levels.

According to yet another aspect, the present invention provides a composition as described herein, for use in treating a disorder and/or medical condition selected from the group consisting of renal insufficiency, renal failure, hyperphosphatemia and/or metabolic acidosis, calcium phosphate deposition, calcification of soft tissue, kidney stones, and elevated serum calcium levels.

The pharmaceutical compositions of the present invention may be administered at a dose of about 10 to about 500 mg/kg/day of ferric citrate, for example about 50 to about 400 mg/kg/day, preferably about 100 to about 300 mg/kg/day. It is contemplated that the dose at which the pharmaceutical composition is administered comprises an amount effective to achieve its intended purpose. The actual amount effective for a particular application will depend, inter alia, on the condition being treated. The dosage and frequency (single or multiple doses) of the pharmaceutical composition can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Additional factors include, but are not limited to, potency, relative bioavailability, presence and severity of adverse side effects, preferred mode of administration, and the toxicity profile. Doses and frequency may be initially determined in vitro, for example from cell culture assays or in vivo using various animal models.

As used herein and in the appended claims the singular forms "a", "an" and "the" include plural references unless the context clearly dictates otherwise. Thus, for example, reference to "a layer" includes a single layer or plurality of such layers and equivalents thereof known to those skilled in the art, and so forth.

The principles of the present invention are demonstrated by means of the following non-limiting examples.

EXAMPLES

Example 1: Process for Preparing Ferric Citrate Tablets without Applying the Ferric Citrate Solution onto Inert Cores (a) Milling Ferric citrate was milled using Clit mill (hammers) with 500 micron sieve in (i) 1,000 rpm or (ii) 4,500 rpm to form a fine powder.

The particle size measured for (i) was less than about 300 microns (about 40% of the particles had a particle size of less than about 75 microns). The particle size measured for (ii) was less than about 250 microns (about 60% of the particles had a particle size of less than about 75 microns).

(b) Blending Milled Ferric Citrate

The following substances were homogenously blended (Table 1):

TABLE 1

| Substance | gr |
| --- | --- |
| Milled Ferric Citrate (i) or (ii) | 450.0 |
| Povidone K-30 | 18.0 |
| Crospovidone XL 10 | 29.2 |
| AVICEL ® 102/microcrystalline cellulose | 72.3 |
| Silicon dioxide/colloidal silicon dioxide | 2.9 |
| Sodium stearyl fumarate | 11.7 |

(c) Tableting:

The blend from (b) was compressed into 1,560 mg tablets, with the following composition (Table 2):

TABLE 2

| Substance | mg/tab | % |
| --- | --- | --- |
| Milled Ferric citrate (i) or (ii) | 1201.9 | 77.0 |
| Microcrystalline cellulose PH102 | 193.0 | 12.4 |
| Povidone K 30 | 48.1 | 3.1 |
| Crospovidone | 78.0 | 5.0 |
| Colloidal silicon dioxide | 7.8 | 0.5 |
| Sodium stearyl fumarate | 31.2 | 2.0 |
| Total | 1560.0 | 100.0 |

In most instances, it was impossible to obtain tablets from the blend of milled ferric citrate (i) due to capping (i.e., partial or complete separation of the top or bottom of the tablet).

Example 2: In Vitro Dissolution Test

Dissolution testing was conducted to the pharmaceutical composition prepared according to Example 1. Testing was performed on entire uncapped tablets. The following conditions were used:

Dissolution instrument: Distek Evolution 6100

Medium: pH 4.0 McIlvaine buffer

Apparatus USP: Apparatus II (paddle method); 100 rpm

Temperature: 37° C.±0.5° C.

Time: Samples taken at 15 and 45 minutes

UV-VIS Instrument: Agilent 8453 UV-VIS; 360 nm with 600 nm background

The Dissolution results for tablets pressed with (ii) were 46% dissolved in 15 min and 72% dissolved in 45 min.

Example 3: Tableting of Unmilled Ferric Citrate

Unmilled Ferric citrate was homogenously blended with the same excipients as described in table (1), and pressed into tablets with the same composition as described in table (2).

It was impossible to obtain tablets from the blend of unmilled ferric citrate due to capping.

Example 4: Process for Preparing Ferric Citrate Tablets According to Embodiments of the Present Invention (a) Preparing the Granules:

1.60 kg of ferric citrate and 0.64 kg PVP K-30/povidone were dissolved in 3.2 Liter hot purified water (80° C.) to attain a visually clear solution. The solution was then applied onto pre-heated 1.50 kg of AVICEL® 101/microcrystalline cellulose using spray coating in fluid bed coater TURBOJET. Additional clear solutions containing 1.60 kg of ferric citrate and 0.64 kg PVP K-30/povidone dissolved in 3.2 Liter hot purified water (80° C.) were repeatedly applied onto the thus formed granules until gaining a ferric citrate content of at least 80%. To avoid solidification of the product, the solution was kept heated above 80° C. and stirred throughout the process.

Process parameters:

Inlet air temp: 40-60° C.

Product temp: 30-40° C.

Outlet air temp: 35-45° C.

Solution spray rate: 3-30 g/min

Nozzle diameter: 0.8 mm

Atomizing pressure: 1-2 bar (b) Milling:

The final granules were milled using Clit mill (hammers) with 500 micron sieve to form a powder. The mean particle size measured was less than about 400 microns. Furthermore, about 50% of the particles had a particle size of less than about 75 microns.

(c) Blending the Milled Granules with Pharmaceutically Acceptable Excipients:

The following substances were homogenously blended (Table 3):

TABLE 3

| Substance | gr |
|---|---|
| Milled Ferric citrate granules | 1781.7 |
| Crospovidone XL 10 | 108.8 |
| AVICEL ® 102/microcrystalline cellulose | 231.1 |
| Silicon dioxide/colloidal silicon dioxide | 10.9 |
| Sodium stearyl fumarate | 43.5 |

(d) Tableting:

The blend from (c) was compressed into 1,360 mg tablets, with the following composition (Table 4):

TABLE 4

| Substance | mg/tab | % |
|---|---|---|
| Granulate: | | |
| Ferric citrate | 1000.0 | 73.5 |
| Microcrystalline cellulose PH101 | 73.6 | 5.4 |
| Povidone K 30 | 40.0 | 3.0 |
| Total granulate | 1113.6 | 81.9 |
| Microcrystalline cellulose PH102 | 144.4 | 10.6 |
| Crospovidone | 68.0 | 5.0 |
| Colloidal silicon dioxide | 6.8 | 0.5 |
| Sodium stearyl fumarate | 27.2 | 2.0 |
| Total | 1360.0 | 100.0 |

The tablets are characterized by the following parameters: Hardness 180-260 N; friability 0.3%; disintegration <45 sec.

(e) Coating Process:

TABLE 5

| Substance | gr | % |
|---|---|---|
| HPMC based coating | 150 | 15 |
| Purified Water | 850 | 85 |
| Total | 1000 | 100 |

1,000 gr tablets were charged into a fully perforated pan coater. The coating solution was applied onto the tablets using spray coating. When a weight gain of 2-5 wt % was reached, the tablets were dried.

Coating Parameters:
Inlet air temp: 45-60° C.
Outlet air temp: 32-40° C.
Pan RPM: 6-12
Air flow: 100-200 cfm
Nozzle diameter: 0.8 mm
Atomizing air: 0.8-1.5 bar Coating adds 2-5% to the weight of the core (1,360 mg).

Example 5: In Vitro Dissolution Test

Dissolution testing was conducted to the pharmaceutical composition prepared according to Example 4. The following conditions were used:

Dissolution instrument: Distek Evolution 6100
Medium: pH 4.0 McIlvaine buffer
Apparatus USP: Apparatus II (paddle method); 100 rpm
Temperature: 37° C.±0.5° C.
Time: Samples taken at 15 minutes
UV-VIS Instrument: Agilent 8453 UV-VIS; 360 nm with 600 nm background The dissolution result for the tablets obtained after applying the ferric citrate solution onto inert cores (Example 4) was 98% dissolution in 15 min As can be seen from the dissolution result, the ferric citrate tablets obtained after applying the ferric citrate solution onto inert cores (Example 4) showed a surprising higher dissolution rate than the reference ferric citrate tablets (Examples 1 and 2).

Example 6: BET Surface Area Analysis

A BET analysis was conducted according to the standards set forth in the United States Pharmacopeia (USP), the results of which are depicted in Table 6:

TABLE 6

| Product | BET active surface area results ($m^2/g$) |
|---|---|
| Milled coated granules (inert core coated with ferric citrate and a binder) | 2.745 |

Example 7: Process for Preparing Ferric Citrate Tablets According to Embodiments of the Present Invention (a) Preparing the Granules:

0.601 kg of ferric citrate and 0.024 kg PVP K-30/povidone were dissolved in 1.202 Liter of hot purified water (80° C.) to attain a visually clear solution. The solution was then applied onto pre-heated 0.541 kg of AVICEL® 101/microcrystalline cellulose using spray coating in fluid bed coater GLATT GPCG-1. Additional clear solutions containing 0.601 kg of ferric citrate and 0.024 kg PVP K-30/povidone dissolved in 1.202 Liter hot purified water (80° C.) were repeatedly applied onto the thus formed granules until gaining a ferric citrate content of at least 80%. To avoid solidification of the product, the solution was kept heated above 80° C. and stirred throughout the process.

Process Parameters:
Inlet air temp: 40-60° C.
Product temp: 30-40° C.
Outlet air temp: 35-45° C.
Solution rate: 3-10 g/min
Nozzle diameter: 1.0 mm
Atomizing pressure: 1-2 bar (b) Milling:

The final granules were milled using Clit mill with 500 micron sieve to form a powder. The mean particle size measured was less than about 400 microns. Furthermore, about 50% of the particles had a particle size of less than about 75 microns.

(c) Blending the Milled Granules with Pharmaceutically Acceptable Excipients:

The following substances were homogenously blended (Table 7):

TABLE 7

| Substance | gr |
|---|---|
| Milled Ferric citrate granules | 1000.0 |
| AVICEL ® 102/microcrystalline cellulose | 40.2 |
| Crospovidone (Kollidon CL) | 85.2 |
| PVP K-30 | 60.8 |
| Silicon dioxide/colloidal silicon dioxide | 6.1 |
| Sodium stearyl fumarate | 24.3 |

(d) Tableting:

The blend from (c) was compressed into 1,406 mg tablets, with the following composition (Table 8):

TABLE 8

| Substance | mg/tab | % |
|---|---|---|
| Granulate: | | |
| Ferric citrate | 1054.5 | 75.0 |
| Microcrystalline cellulose PH101 | 4.3 | 0.3 |
| Povidone K 30 | 50.8 | 3.6 |
| Total granulate: | 1109.6 | 78.9 |
| Microcrystalline cellulose PH102 | 43.6 | 3.1 |
| Crospovidone (Kollidon CL) | 94.2 | 6.7 |
| PVP K-30 | 125.1 | 8.9 |
| Silicon dioxide/colloidal silicon dioxide | 7.0 | 0.5 |
| Sodium stearyl fumarate | 26.7 | 1.9 |
| Total | 1406.2 | 100 |

The tablets are characterized by the following parameters: Hardness 100-130 N; friability 0.4%; disintegration <30 min.

Example 8: In Vitro Dissolution Test

Dissolution testing was conducted to the pharmaceutical composition prepared according to Example 7. The following conditions were used:

Dissolution instrument: VanKel SN 1-3148-1093
Medium: pH 4.0 McIlvaine buffer
Apparatus USP: Apparatus II (paddle method); 100 rpm
Temperature: 37° C.±0.5° C.
Time: Samples taken at 15 minutes
UV-VIS Instrument: Agilent 8453 UV-VIS; 360 nm The dissolution result for the tablets obtained after applying the ferric citrate solution onto inert cores (Example 7) was 96% dissolution in 15 min As can be seen from the dissolution result, the ferric citrate tablets obtained after applying the ferric citrate solution onto inert cores (Example 7) showed a surprising higher dissolution rate than the reference ferric citrate tablets (Examples 1 and 2).

Example 9: Stability Test

Tablets prepared according to Example 7 were placed in stability testing in 2 conditions: A) accelerated conditions (40° C., 75% relative humidity), and B) room temperature conditions (25° C., 60% relative humidity). In particular, tablets were packaged in aluminum blisters which were stored at the different storage conditions for a total of 3 months. Few blisters were taken out of the accelerated conditions incubator at three time points: 1 month, 2 months and 3 months. Blisters were taken out of the room temperature conditions incubator at 3 months. The dissolution profile of the tablets was determined as described hereinabove. Results showed that the formulation of the present invention was stable under conditions tested, with dissolution higher than 90% after 15 min in all storage conditions.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A solid pharmaceutical composition comprising:
    (a) granules comprising an inert core and a layer over said core,
    wherein the weight ratio between the inert core and the layer over said core is about 1:8 to 1:300, and said layer comprises ferric citrate in an amount of at least about 50 wt % based on the total weight of said solid pharmaceutical composition, and optionally a binder; and
    (b) optionally, at least one pharmaceutically acceptable excipient;
    wherein upon compression the obtained tablet is characterized by having friability of less than about 1% and an in vitro dissolution profile in which at least about 90% of the drug is released from the composition within about 15 minutes, wherein the in vitro dissolution profile is measured in a type II Paddle dissolution apparatus in McIlvaine buffer 98% (pH 4.0) or in EDTA solution.

2. The composition according to claim 1, wherein the granules are milled.

3. The composition according to claim 1, wherein the inert core comprises microcrystalline cellulose.

4. The composition according to claim 1, wherein the composition contains at least one pharmaceutically acceptable excipient as an intra-granular excipient, an extra-granular excipient, or a combination thereof, and wherein said pharmaceutically acceptable excipient is selected from the group consisting of a binder, a disintegrating agent, a filler, an anti-tacking agent, a lubricant, a glidant, a surfactant, a plasticizer and any combination thereof.

5. The composition according to claim 4, wherein said composition comprises a filler which is microcrystalline cellulose.

6. The composition according to claim 1, which is prepared by the steps of (i) applying a solution or dispersion comprising ferric citrate and optionally a binder over said inert core so as to obtain granules; (ii) optionally milling the granules to obtain milled granules; (iii) optionally blending said granules with at least one pharmaceutically acceptable excipient to obtain a blend; and (iv) optionally compressing the granules of step (i) or the milled granules of step (ii) or the blend of step (iii) to obtain a tablet.

7. The composition according to claim 6, wherein step (i) comprises spray coating.

8. The composition according to claim 1, which is in a form suitable for oral administration selected from the group consisting of a tablet, a capsule, a pill, a powder, and a pellet, or which is in a form suitable for oral administration comprising a powder, wherein the composition is mixed with a liquid to form a suspension or solution prior to administration.

9. The composition according to claim 1 in the form of a tablet, further comprising at least one coating layer over the tablet.

10. The composition according to claim 9, wherein said coating layer over the tablet is an immediate release coating.

11. The composition according to claim 1, comprising residual amount of water in an amount of about 1-20% by weight of the composition.

12. The composition according to claim 1, having a BET (Brunauer Emmett Teller) active surface area of less than about 10 sq. m/g.

13. A method for preparing a solid pharmaceutical composition according to claim 1, the method comprising the steps of:
  (a) dissolving or dispersing ferric citrate and optionally a binder in an aqueous medium to obtain a solution or dispersion;
  (b) applying the solution or dispersion obtained in step (a) onto an inert core so as to obtain granules;
  (c) optionally milling the granules to obtain milled granules;
  (d) optionally drying the granules of step (b) or the milled granules of step (c) to obtain dry granules;
  (e) optionally blending the granules of step (b) or the milled granules of step (c) or the dry granules of step (d) with at least one pharmaceutically acceptable excipient to obtain a blend; and
  (f) optionally compressing the granules of step (b) or the milled granules of step (c) or the dry granules of step (d) or the blend of step (e) to obtain a tablet.

14. The method according to claim 13, wherein the aqueous medium is hot water at a temperature of between about 40° C. to about 80° C.

15. The method according to claim 13, wherein step (f) is performed, the method further comprising a step (g) of applying at least one coating layer onto said tablet.

16. The method according to claim 13, wherein step (c) is performed to form a powder having a mean particle size of less than about 400 microns.

17. The method according to claim 13, wherein step (d) is performed.

18. The method according to claim 13, wherein step (e) is performed and wherein said at least one pharmaceutically acceptable excipient is intra-granular, extra-granular, or a combination thereof.

19. A method for treating a disorder or a medical condition selected from the group consisting of renal insufficiency, renal failure, hyperphosphatemia, metabolic acidosis, calcium phosphate deposition, calcification of soft tissue, kidney stones, elevated serum calcium levels and anemia, the method comprising the step of administering to a subject in need thereof a pharmaceutical composition according to claim 1.

20. The method according to claim 19, wherein the administration route is oral.

21. The composition according to claim 1, wherein the composition contains a binder which is povidone (PVP).

22. The composition according to claim 4, wherein said composition comprises a disintegrating agent which is crospovidone.

23. The composition according to claim 4, wherein said composition comprises a glidant which is colloidal silicon dioxide.

24. The composition according to claim 4, wherein said composition comprises a lubricant which is sodium stearyl fumarate.

* * * * *